United States Patent [19]

Cipollina et al.

[11] Patent Number: 5,583,149
[45] Date of Patent: Dec. 10, 1996

[54] ANTIMIGRAINE DERIVATIVES OF INDOLYLCYCLOALKANYLAMINES

[75] Inventors: Joseph A. Cipollina, Middletown; Jonas A. Gylys, Southington; Ronald J. Mattson, Meriden; Charles P. Sloan, Wallingford, all of Conn.

[73] Assignee: Bristol-Myers Squibb Company, New York, N.Y.

[21] Appl. No.: 517,525

[22] Filed: Aug. 21, 1995

Related U.S. Application Data

[62] Division of Ser. No. 178,079, Jan. 6, 1994, Pat. No. 5,468,768.

[51] Int. Cl.$^6$ .................. A61K 31/44; C07D 401/10
[52] U.S. Cl. .................. 514/339; 514/256; 514/269; 514/415; 544/242; 544/298; 544/319; 544/330; 544/333; 546/273; 546/277.4; 548/469; 548/509; 548/510; 548/511
[58] Field of Search .................. 548/469, 509, 548/510, 511; 514/415, 339, 256, 269; 546/273; 544/242, 298, 319, 330, 333

[56] References Cited

U.S. PATENT DOCUMENTS

| | | | |
|---|---|---|---|
| 3,238,215 | 3/1966 | Zenitz | 260/293 |
| 4,252,803 | 2/1981 | Webb | 424/248.5 |
| 4,954,502 | 9/1990 | Smith et al. | 548/469 |
| 5,124,332 | 6/1992 | Wise et al. | 548/469 |

FOREIGN PATENT DOCUMENTS

| | | |
|---|---|---|
| 2059708 | 7/1992 | Canada . |
| 464558 | 1/1992 | European Pat. Off. . |
| 0548813 | 6/1993 | European Pat. Off. . |
| 0560669 | 9/1993 | European Pat. Off. . |
| 2458550 | 1/1981 | France . |
| 2162522 | 2/1986 | United Kingdom . |
| 2124210 | 2/1994 | United Kingdom . |
| WO92/13856 | 8/1992 | WIPO . |
| WO92/15302 | 9/1992 | WIPO . |
| WO92/15303 | 9/1992 | WIPO . |
| WO93/10092 | 5/1993 | WIPO . |
| WO93/11106 | 6/1993 | WIPO . |

OTHER PUBLICATIONS

Chemical Abstracts, vol. 65, No. 5, Aug. 29, 1966.
Glennon et al, "5–HT1D Serotonin Receptors: Results of a Structure–Affinity Investigation," Drug Development Research, vol. 22, 1991, pp. 25–36.

Primary Examiner—Joseph McKane
Attorney, Agent, or Firm—Richard P. Ryan

[57] ABSTRACT

A series of novel serotonergic indolyl derivatives of cycloalkanyl- and cycloalkenyl-amines of Formula I are intended for use in the alleviation of vascular headaches.

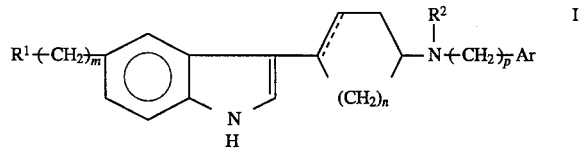

8 Claims, No Drawings

ANTIMIGRAINE DERIVATIVES OF INDOLYLCYCLOALKANYLAMINES

CROSS-REFERENCE TO RELATED APPLICATION

This is a division of application U.S. Ser. No. 08/178,079 filed Jan. 6, 1994 now U.S. Pat. No. 5,468,768.

BACKGROUND OF THE INVENTION

This invention generally pertains to heterocyclic carbon compounds having drug and bio-affecting properties and to their preparation and use. In particular, the invention is concerned with disubstituted cycloalkanyl and cycloalkenyl derivatives wherein one substituent moiety is a 5-substituted indol-3-yl group and the other moiety is an aryl or a heteroaryl, e.g. pyridinyl, ring. These compounds possess a unique serotonergic profile that renders them, inter alia, useful in treatment of vascular headaches such as migraine or cluster type.

Dowie, et al. disclosed a series of 3-alkylamino-indole derivatives as being potentially useful for the treatment of migraine in a published patent application, GB 2,124,210. One member of this series of compounds was specifically claimed in a later patent application of Oxford, GB 2,162,522, published Feb. 5, 1986. This particular compound is known in the literature as sumatriptan(i).

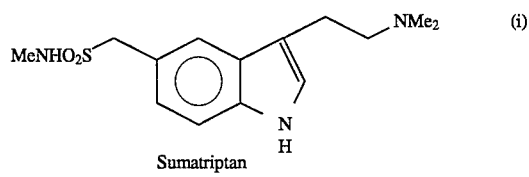

Sumatriptan

A number of sumatriptan derivatives comprising variations in the 5-indolyl-substituent have been disclosed, e.g. WO 9311106 by Macor; as well as disclosures of variations in the 3-indolyl-alkylamino substituent, e.g. WO 9213856 by Nowakowski.

Structural variations involving replacement of the dialkylamino moiety by incorporation of a piperazinyl ring system to give compounds of formula (ii) have been disclosed.

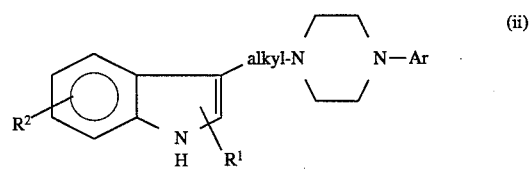

Compounds of formula (ii) are known wherein Ar is a pyridine ring (U.S. Pat. No. 4,954,502 to Smith, et al.); an optimally substituted phenyl ring (Canadian patent application 2,059,708 by Bottcher, et al.); and a pyrimidinyl system (EP 0548813A by Smith, et al.).

Related hydropyridine compounds of formula (iii) have also

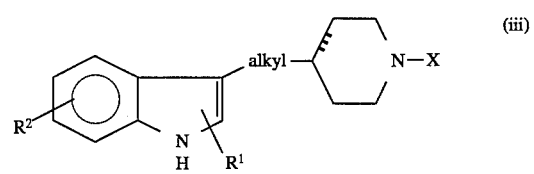

been synthesized and disclosed as antipsychotics (FR 2458550); anti-dementia agents (WO 9215303 by Perrigaard, et al.) and agents for treating substance abuse (WO 9215302 by Perrigaard, et al.).

More closely related, at least in terms of molecular structure, are compounds of formula (iv) which have been

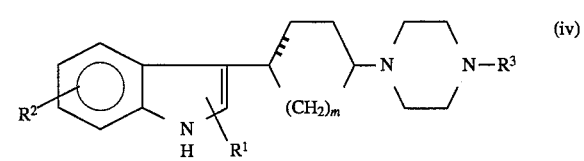

disclosed as dopaminergic agents for treating psychosis (U.S. Pat. No. 5,124,332 to Wise, et al. and WO 9310092 by Caprathe, et al.); and cerebral ischemia (EPO-A 0560669 by Mattson, et al.).

None of the foregoing references, either singly or in combination, teach or suggest the particular combination of structural variants comprising the novel compounds of the present invention nor their use as serotonergic agents with particular utility in treating migraine headache.

Migraine is a member of a broader class of headache that also comprises cluster headaches and other headaches believed to have a vascular implication in their etiology. These headaches are often classified as vascular headaches. For a current summary of headache and its treatment see: Chapter 13: "Drugs Used to Treat Migraine and Other Headaches" in *Drug Evaluations*, 6th Edn., 1986, pages 239–253 American Medical Association, W. B. Saunders Co., Philadelphia, Pa.

Frequent irregularly-occurring episodes of headache afflict a large number of people but are usually acute in nature and of short duration. Relief of this type of headache is typically provided by mild analgesics such as aspirin or acetaminophen. Such headaches are quite common and, while painful and perhaps annoying, are seldom incapacitating and debilitating. Chronic recurrent headaches of the vascular category, however, usually lead to patent consultation with a physician due to pain severity which is often incapacitating.

Although there is no universally accepted classification system for headache, vascular headache, for the proposes of the present invention, refers mainly to migraine and cluster headaches. Migraine includes the common or classical type as well as migraine variants which would be familiar to one skilled in the art. Other subtypes such as toxic vascular and hypertensive headaches, chronic paroxysmal hemicrania, as well as some muscle-contraction and combined or mixed vascular-muscle headaches may also fall into a vascular-related headache category and be treatable by the present invention. It is appreciated by one skilled in the art that no single therapy is effective in all patients diagnosed with the same subtype of headache, thereby raising further uncertainties about headache classification.

The present invention relates to novel indolyl-cycloalkanyl and cycloalkenyl derivatives of arylalkylamines, their therapeutic use as serotonergic agents, particularly in headache therapy and their pharmaceutical compositions.

SUMMARY AND DETAILED DESCRIPTION OF THE INVENTION

The method of use of the present invention is intended for the alleviation of vascular or vascular-related headache of which migraine and cluster headache are the best known specific examples. The method essentially involves administration of a substituted indol-3-yl derivative of an N-alkyl-N-cycloalkanyl or cycloalkenyl amine, or a pharmaceutically acceptable salt and/or solvate thereof, to a human in need of such treatment. For use in the instant method, oral and transnasal administration of pharmaceutical compositions containing the subject serotonergic agents are preferred.

In a broad aspect, the present invention is concerned with substituted indol-3-yl derivatives of cycloalkanyl and cycloalkenyl amines having useful serotonergic properties and characterized by Formula I.

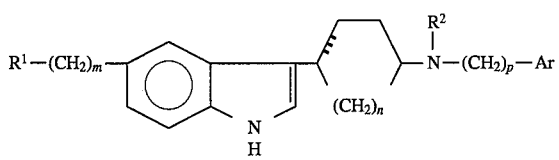

In Formula I, $R^1$ is a substituent selected from —$COR^2$; —$CONHR^3$; —$CO_2R^4$; —OH; —$NR^2COR^4$; —$NR^2SO_2R^3$; —$SO_2R^4$; and —$SO_2NHR^3$.

Ar is

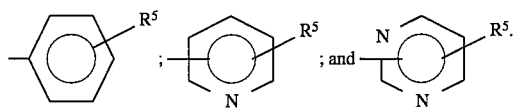

$R^2$ can be hydrogen and lower alkyl. $R^3$ can be hydrogen, lower alkyl, and phenyl-lower-alkylene. $R^4$ is lower alkyl; and $R^5$ can be hydrogen, halogen, and lower alkoxy.

The symbol m is zero or 1; n is an integer from 1 to 3; and p is zero or an integer from 1 to 4.

Finally, the solid plus dotted line is meant to represent either a single or a double covalent bond.

Additionally, compounds of Formula I also encompass all pharmaceutically acceptable acid addition salts and/or solvates thereof. The present invention is also considered to include stereoisomers including geometric as well as optical isomers, e.g. mixtures of enantiomers as well as individual enantiomers and diastereomers, which arise as a consequence of structural asymmetry in certain compounds of the instant series. Separation of the individual isomers is accomplished by application of various methods which are well known to practitioners in the art.

The term "lower alkyl" refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl, 2-methylpropyl. The term "lower alkoxy" denotes an alkoxy group containing from 1 to 4 carbons, e.g. a methoxy group, a propoxy group, etc. "Lower alkylene-phenyl" refers to phenalkyl groups having alkanyl links of from 1 to 4 carbons. "Halogen" is fluorine, chlorine, bromine, or iodine.

Preferred compounds are those wherein $R^1$ is carboxamide; the cycloalkane and cycloalkene systems are $C_6$-rings (i.e. n is 2); Ar is a phenyl moiety; and p is 2. $R^2$ is also hydrogen in preferred compounds.

The pharmaceutically acceptable acid addition salts of the invention are those in which the counter ion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid, preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and others.

The compounds of formula I can be prepared by adaptation of the general synthetic processes shown in Schemes 1 and 2. In Scheme 1, an appropriately substituted indole (III) is condensed with a cycloalkanone intermediate of formula II to give the cycloalkenyl product IB. Reduction of IB provides the cycloalkanyl product IA.

Scheme 2 sets forth the general method for synthesis of the cycloalkanone intermediates (II). Reductive amination of an appropriate cycloalkanedione-mono-ethylene ketal (VI) and an amine (V) using a reagent such as sodium triacetoxyborohydride affords ketal-amine intermediates of formula IVa. A second reductive amination, if desired, of IVa and an appropriate aldehyde gives the ketal-amine intermediate IVb with $R^2$ being lower alkyl. Removal of the ketal group under acidic conditions gives the cycloalkanone-amine intermediate (II) in high yields.

Scheme 1

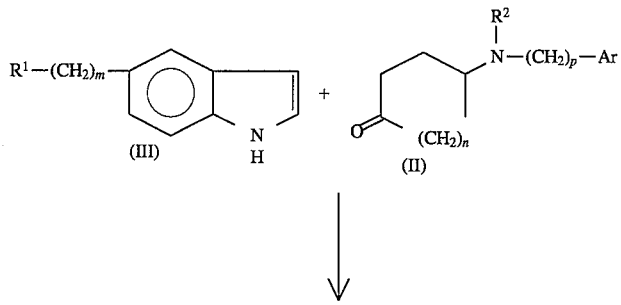

-continued
Scheme 1

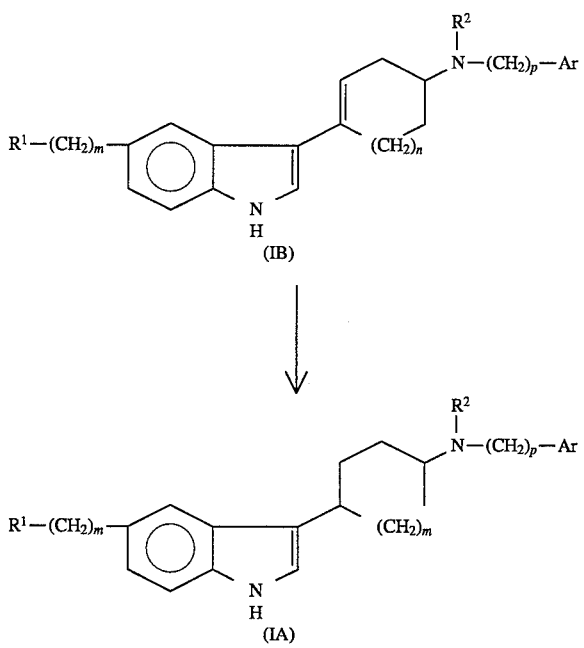

Scheme 2

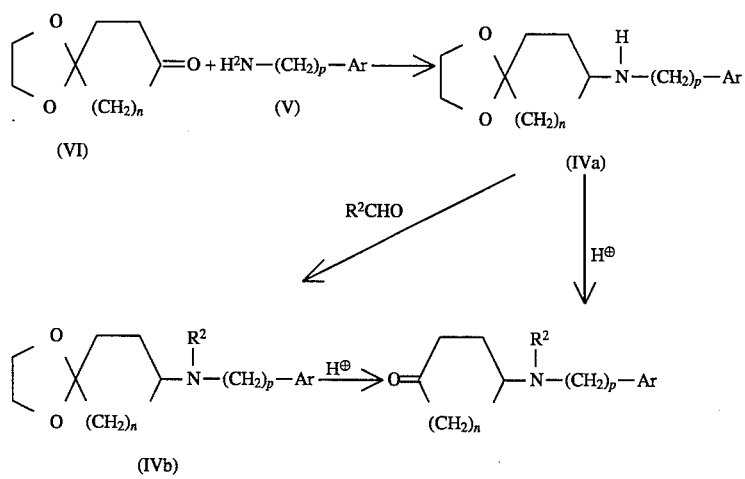

The reactions employed in Schemes 1 and 2 and their application are familiar to the practitioner skilled in organic synthesis and modifications of conditions and reagents would be readily understood. The skilled synthetic chemist would know how to adapt these processes for preparation of specific Formula I compound including other compounds embraced by this invention but not specifically disclosed. Variations of the methods to produce the same compounds in somewhat different fashion will also be evident to one skilled in the art. To provide greater detail in description, representative synthetic examples are provided infra in the "Specific Embodiments" section.

The compounds of Formula I show potent affinity at $5\text{-HT}_1$ binding sites and can be envisioned as potential agents for disorders associated with dysfunction in serotonergic neurotransmission. Such disorders may include depression, anxiety, eating disorders, obesity, drug abuse, and headache. In particular, the active compounds of the instant series are envisioned as specific agents for treating headache of vascular origin.

Serotonin has been linked to the pathophysiology of migraine by accumulating evidence including increased excretion of serotonin metabolites following a migraine attack and a reduction in the serotonin content of blood platelets during the migraine headache. This latter effect appears to be specific for migraine and not a result of pain or stress. (Anthony, et all., "Plasma Serotonin in Migraine and Stress," *Arch. Neurol.* 1967, 16: 544–552). More importantly, intramuscular injection of reserpine lowers plasma serotonin and induces a typical migraine-type headache in migraine sufferers. This induced headache can be alleviated by slow I.V. injection of serotonin creatinine sulfate. (Kimball, et all. "Effect of Serotonin in Migraine Patients," *Neurology N.Y.*, 1960, 10: 107–111).

Although serotonin has been shown to be effective in treating migraine attacks, its use in migraine is precluded by its side-effects such as restlessness, nausea, faintness, hyperpnea, facial flushing and parasthesias. (Lance, et al., "The Control of Cranial Arteries by Humoral Mechanisms and Its Relation to the Migraine Syndrome," *Headache*, 1967, 7: 93–102). For this reason, more specific serotonin agents, which would treat the migraine without all of the other actions, are potentially useful antimigraine medicaments. Accumulating findings have led to the perception that compounds with selectivity for the 5-HT$_{1D}$ sub-type of serotonin receptors would be clinically efficacious in the treatment of migraine. In this regard, the compounds of the instant invention demonstrate potent affinity and agonist activity at the 5-HT$_{1D}$ site. Formula I compounds of interest have potencies wherein IC$_{50}$ values of these compounds at 5-HT$_{1D}$ sites are less than 100 nmolar. Preferred compounds have IC$_{50}$ values below 10 nmolar.

Determination of 5-HT$_{1D}$ binding properties was accomplished employing methodology such as that described by Heuring and Peroutka, *J. Neurosci.*, 7(3), 1987, 894–903; with only minor modifications. In vitro IC$_{50}$ (nM) test values were determined for the compounds of this invention employing tritiated serotonin.

In addition to the 5-HT$_{1D}$ binding test data, ability of the compounds of this invention to elicit contraction in a canine saphenous vein model further indicates usefulness in treating vascular headaches. Preferred compounds of this invention demonstrate potency equal to or in excess of serotonin itself. Selected compounds of the instant series were tested in an in vivo model where they demonstrated effective reduction of carotid blood flow in anesthetized dogs. All these foregoing pharmacologic tests indicate useful antimigraine action for the compounds of this invention.

Another aspect then of the instant invention provides a method for treating a migraine sufferer which comprises systemic administration to the sufferer of a therapeutically effective amount of a compound of Formula I or a pharmaceutically acceptable salt thereof.

The administration and dosage regimen of compounds of Formula I is considered to be done in the same manner as for the reference compound sumatriptan, cf: Oxford, GB 2,162, 522A. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably to about 5 to 20 mg/kg, when administered orally. In some instances, a sufficient therapeutic effect can be obtained at lower doses while in others, larger doses will be required. Systemic administration refers to oral, intra-nasal, rectal and parenteral (i.e. intramuscular, intravenous and subcutaneous). Generally, it will be found that when a compound of the present invention is administered orally, a larger quantity of the active agent is required to produce the same effect as a smaller quantity given intra-nasally or parenterally. In accordance with good clinical practice, it is preferred to administer the instant compounds at a concentration level that will produce effective antimigraine effects without causing any harmful or untoward side effects.

The compounds of the present invention may be administered for antimigraine purposes either as individual therapeutic agents or a mixture with other therapeutic agents. Therapeutically, they are generally given as pharmaceutical compositions comprised of an antimigraine amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for intra-nasal and parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), heptet (hept), quartet (q), triplet (t) or doublet (d). Abbreviations employed are DMSO-d$_6$ (deuterodimethylsulfoxide), CDCl$_3$ (deuterochloroform) and are otherwise conventional. The infrared (IR) spectral descriptions include only absorption wave numbers (cm$^{-1}$).

Analytical thin-layer chromatography (TLC) was performed on 0.25 mm EM silica gel 60 F-254 coated glass plates and preparative flash chromatography was performed on EM silica gel (36–62 µm). The solvent systems used are reported where appropriate. All reaction, extraction and chromatography solvents were reagent grade and used without further purification except tetrahydrofuran (THF) which was distilled from sodium/benzophenone ketyl. All non-aqueous reactions were carried out in flame-dried glassware under a nitrogen atmosphere.

A. Synthesis of Intermediates

Compounds of Formula II

General Procedure

Equivalent amounts of a cycloalkanedione mono-ethylene ketal (VI) and an amine (V) are combined in methylene chloride under N$_2$ at room temperature. A reaction solvent volume of approximately 400 mL CH$_2$Cl$_2$ per 25 gram amounts of VI and V is the amount generally employed. Sodium triacetoxyborohydride (1.25 to 1.50 equivalent per one equivalent of amine) is added in portions, taking care to avoid boilover. The reaction is stirred until TLC examination indicates consumption of starting materials. The reaction is then cooled in an ice-water bath and made basic by the addition of 3 N NaOH. The layers are separated and the aqueous phase is extracted with CH$_2$Cl$_2$ (2×). The organic fractions are collectively dried over Na$_2$SO$_4$, filtered, and the solvent is removed in vacuo. The crude product (IV), which is usually quite clean, is hydrolyzed without further purification.

A variation can be made by converting an IVa intermediate to an IVb intermediate as shown in Scheme 2. For example, an IVa compound wherein R$^2$ is Et, Ar is Ph, n is 2 and p is 2; can be converted in 99% crude yield to the appropriate IVb intermediate by reaction with an equivalent of acetaldehyde and excess NaBH(OAc)$_3$ in methylene chloride.

The crude ketal (IV) is dissolved in 50% H$_2$SO$_4$ (10 mL/g ketal) at room temperature. An equivalent volume of THF is added and the reaction is allowed to stir at room temperature for 18 h. The reaction is cooled is an ice-water bath and, with vigorous stirring, is made strongly basic by the dropwise addition of 50% NaOH. The supernatant is decanted into a separatory funnel and the layers are separated. The aqueous layer is repeatedly extracted with diethyl ether (~5×) with warm water being added to prevent further salt precipitation. The combined organic fractions are back-extracted with brine, dried over MgSO$_4$, filtered and the solvents are removed in vacuo. The crude products are purified by bulb-to-bulb distillation under vacuum (see Table 1).

TABLE 1

Synthesis of Aminocycloalkanones of Formula II

| Ex # | R$^2$ | n | p | Ar | bp (°C. at 5–9 mm)$^a$ | % Yield (2 steps) |
|---|---|---|---|---|---|---|
| 1 | H | 2 | 0 | Ph | (mp 116–7) | 98 |
| 2 | H | 2 | 0 | p-F—Ph | (mp 123–4) | 99 |
| 3 | H | 2 | 1 | Ph | 160–70 | 69 |
| 4 | H | 2 | 2 | Ph | 120–30 | 89 |
| 5 | H | 2 | 2 | o-F—Ph | 190–200 | 51 |
| 6 | H | 2 | 2 | p-F—Ph | 180–90 | 52 |
| 7 | H | 2 | 2 | o-OMe—Ph | NP | 99 |
| 8 | H | 2 | 2 | m-OMe—Ph | NP | 96 |
| 9 | H | 2 | 2 | p-OMe—Ph | 190–200 | 52 |
| 10 | H | 2 | 2 | 2-pyridinyl | NP | 55 |
| 11 | H | 2 | 2 | 3-pyridinyl | 190–200 | 50 |
| 12 | H | 2 | 3 | Ph | 180–90 | 63 |

$^a$Compounds were purified by kugelrohr bulb-to-bulb distillation under reduced pressure. Reported temperatures indicate pot temperature at which product was collected. NP = not purified; in these instances, compounds were either clean enough to use in their crude reaction form or they were flash chromatographed.

Compounds of Formula III

Many 5-substituted indoles are known and can be readily prepared from literature procedures with some indoles also being commercially available. However, some of the 5-substituted indoles are more difficult to obtain by standard methodology. However, many of the 5-substituted indoles of Formula III can be conveniently obtained by means of a novel palladium [O] coupling process.

This method is exemplified in several following examples.

EXAMPLE 13

5-[(Methylsulfonyl)methyl]-1H-indole

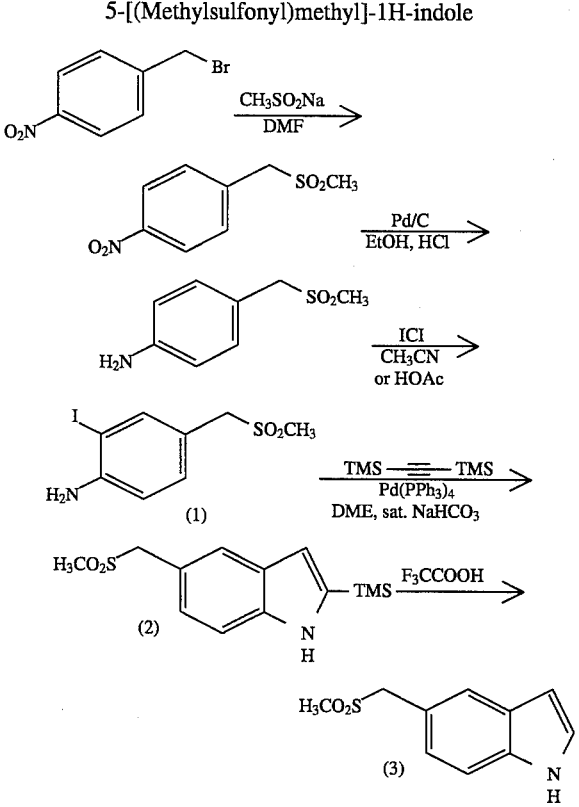

2-Iodo-4-[(methylsulfonyl)methyl]benzenamine (1)

Method A. 4-[(Methylsulfonyl)methyl]benzenamine (10.0 g, 0.054 mol) was dissolved in HOAc (150 mL) followed by the addition of water (20 mL). Iodine monochloride (ICl, 9.65 g, 0.0595 mol) was dissolved in HOAc (15 mL) and added dropwise to the mixture over 15 min. at RT. The mixture was heated to 90° C. for 5 min. and then allowed to cool to RT for 1 h. An aqueous saturated solution of sodium bisulfite (15 mL) was added with stirring. The solvent was concentrated in vacuo. The residue was dissolved in CH$_2$Cl$_2$ and extracted with brine and then with water. The combined organic layers were dried over Na$_2$SO$_4$, filtered and concentrated in vacuo. Silica gel chromatography (10–100% EtOAc gradient in hexane) of the residue afforded the product (1) (7.23 g, 43%) as a brown oil that crystallized upon standing.

Method B. 4-[(Methylsulfonyl)methyl]benzenamine (3.74 g, 0.0202 mol) was dissolved in CH$_3$CN (80 mL) and iodine monochloride (3.45 g, 0.0212 mol) CH$_3$CN (10 mL) was added dropwise over 15 min. at RT.

The mixture was gently heated and then allowed to stir at RT for 1 h. The solvent was concentrated in vacuo. The residue was dissolved in EtOAc and washed with a solution comprised of saturated aqueous Na$_2$CO$_3$ (50 mL) and of saturated aqueous sodium bisulfite (10 mL) and then with water. The organic layer was dried over MgSO$_4$, filtered and concentrated in vacuo to give the crude product (1). Trituration using EtOAc followed by recrystalization from CH$_3$CN gave the product (3.50 g, 55.7%).

5-[(Methylsulfonyl)methyl]-2-(trimethylsilyl)-1H-indole (2)

To a solution of 1,2-dimethoxyethane (DME, 70 mL) was added 2-iodo-4-[(methylsulfonyl)methyl]benzenamine (1) (1.9 g, 0.0061 mol), bis(trimethylsilyl) acetylene (1.56 g, 0.00915 mol), tetrakistriphenylphosphine Pd(O) (0.705 g, 0.00061 mol) and saturated aqueous $Na_2CO_3$ (5 mL). The reaction was heated at reflux for 48 h. The solvent was removed in vacuo and the residue was dissolved in EtOAc and washed with brine. The organic layer was dried over $MgSO_4$, filtered and evaporated to give the crude product. Silica gel chromatography (20–100% EtOAc gradient in hexane followed by 5–10% MeOH gradient in EtOAc) of the concentrate afforded the product (2) (1.42 g, 83%) as a brown oil.

5-[(Methylsulfonyl)methyl]-1H-indole (3)

5-[(Methylsulfonyl)methyl]-2-(trimethylsilyl)-1H-indole (2) (1.5 g, 0.00534 mol) was dissolved in $CH_2Cl_2$ (70 mL). Trifluoroacetic acid (2 mL) was added and the mixture was stirred at RT for 2 h. The solvent was concentrated in vacuo and the residue was dissolved in EtOAc and extracted with sat. $NaHCO_3$ and then with brine. The organic phase was dried over $MgSO_4$, filtered and evaporate in vacuo. Silica gel chromatography (50–100% EtOAc gradient in hexane) of the concentrate gave the product 0.57 g, 51%) as a brown oil.

EXAMPLE 14

5-[(Methylamine)sulfonyl]methyl]-1H-indole

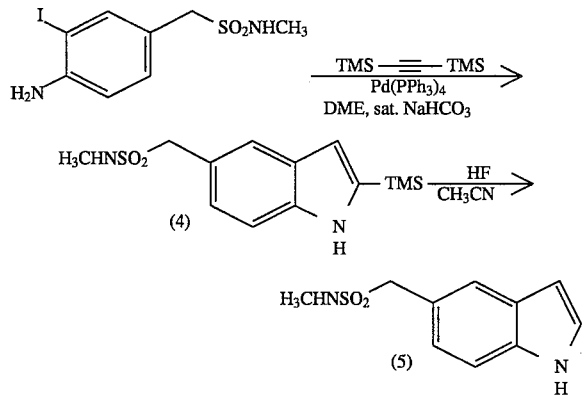

5-[[(Methylamino)sulfonyl]methyl]-2-(trimethylsilyl)-1H-indole (4)

4-Amino-3-iodo-N-methyl-benzenemethanesulfonamide (1.63 g, 0.005 mol), bis(trimethylsilyl)acetylene (1.28 g, 0.0075 mol) and tetrakistriphenylphosphine Pd(O) (0.578 g, 0.0005 mol) were dissolved in DME (50 mL) and followed by the addition of saturated aqueous $Na_2CO_3$ (5 mL). The mixture was heated at reflux for 48 h. The solvent was removed in vacuo. The residue was dissolved in EtOAc and extracted with brine. The organic layer was dried over $Na_2SO_4$, filtered and evaporated in vacuo. Silica gel chromatography (10–100% EtOAc gradient in hexane) of the residue afforded the product (4) (1.08 g, 76.8%).

5-[[(Methylamino)sulfonyl]methyl]-1H-indole (5)

5-[[(Methylamino)sulfonyl]methyl]-2-(trimethylsilyl)-1H-indole (4) ( 1.0 g, 0.00356 mol) was dissolved in $CH_3CN$ (40 mL). Concentrated hydrofluoric acid (HF, 1 mL) was added and the mixture was stirred at RT for 3 h. The solvent was removed in vacuo and the residue was dissolved in EtOAc. The organic phase was extracted sequentially with saturated aqueous $NaHCO_3$ and brine, dried over $MgSO_4$, filtered and concentrated in vacuo. Silica gel chromatography (10–100% EtOAc gradient in hexane) of the residue gave the product (5) (0.52 g, 65.2%).

EXAMPLE 15

N-Methyl-1H-indole-5-acetamide

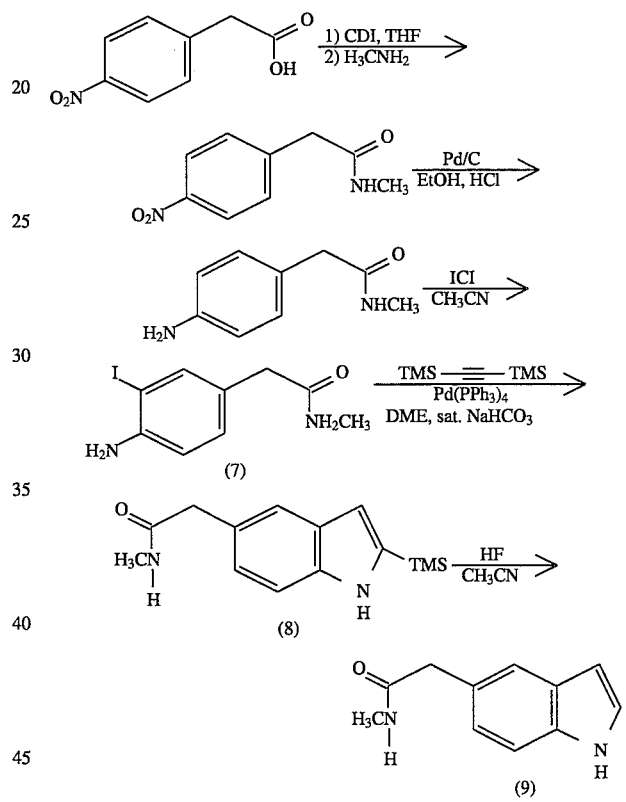

4-Amino-N-methyl-benzeneacetamide (6)

4-Nitrobenzeneacetic acid (16.6 g, 0.0916 mol) was dissolved in THF (200 mL) and carbonyldiimidazole (CDI, 15.6 g, 0.0963 mol) was added. Carbon dioxide evolution rapidly ensued and the reaction mixture was stirred at RT for 30 min. Gaseous methylamine was then bubbled through the mixture until it was distinctly basic to litmus paper. The THF was removed in vacuo and water (70 mL) was added. The solid material was collected by filtration and placed in a Parr bottle were palladium on carbon (10%, 3 g). A solution of EtOH (200 mL) and 1N HCl (50 mL) was added and the mixture was hydrogenated at 60 psi for 4 h. The reaction was filtered, concentrated in vacuo and the residue made basic with saturated aqueous $Na_2CO_3$. The aqueous mixture was extracted with EtOAc. The combined organic layers were washed with brine, dried over $MgSO_4$, filtered and concentrated in vacuo to give the product (6) (10.0 g, 66.6%) which was pure by NMR analysis.

4-Amino-3-iodo-N-methyl-benzeneacetamide (7)

4-Amino-N-methyl-benzeneacetamide (6) (6.56 g, 0.04 mol) was dissolved in $CH_3CN$ (200 mL) and ICl (7.14 g dissolved in 60 mL of $CH_3CN$, 0.044 mol) was added dropwise with vigorous stirring. After stirring at RT for 3 h, saturated aqueous $Na_2CO_3$ (50 mL) was added and the reaction was concentrated in vacuo. The residue was dissolved in EtOAc and extracted with saturated aqueous $Na_2CO_3$. The organic phase was dried over $MgSO_4$, filtered and concentrated in vacuo. The product (7) (7.38 g, 63.6%) was isolated from the concentrate by trituration with $CH_2Cl_2$/EtOAc and washing with $Et_2O$. This material was found to be pure by NMR analysis.

N-Methyl-2-(trimethylsilyl)-1H-indole-5-acetamide (8)

4-Amino-3-iodo-N-methyl-benzeneacetamide (7) (7.26 g, 0.025 mol), bis(trimethylsilyl) acetylene (8.52 g, 0.05 mol) and tetrakistriphenylphosphine Pd(O) (2.89 g, 0.0025 mol) were dissolved in $CH_3CN$ (400 mL) followed by the addition of saturated aqueous $NaHCO_3$ (30 mL). The mixture was heated at reflux for 24 h. The solvent was removed in vacuo and the residue was dissolved in EtOAc. The organic phase was extracted with brine, dried over $MgSO_4$, filtered and concentrated in vacuo. Silica gel chromatography (50–100% EtOAc gradient in hexane) of the concentrate afforded the product (8) (2.52 g, 38.8%) as a yellow viscous oil.

N-Methyl-1H-indole-5-acetamide (9)

N-Methyl-2-(trimethylsilyl)-1H-indole-5-acetamide (8) (2.5 g, 0.00961 mol) was dissolved in $CH_3CN$ (50 mL) and HF (1.9 g of a 50% aqueous solution, 0.048 mol) was added. The mixture was stirred at RT for 1.5 h. The solvent was removed in vacuo and the residue was dissolved in EtOAc. The organic phase was extracted with saturated aqueous $NaHCO_3$ and then with brine, dried over $MgSO_4$, filtered and evaporated in vacuo. Silica gel chromatography (10–100% EtOAc gradient in hexane) of the concentrate afforded the product (0.86 g, 47.6%).

EXAMPLE 16

General Procedure: Secondary Indole-5-Carboxamides (11)

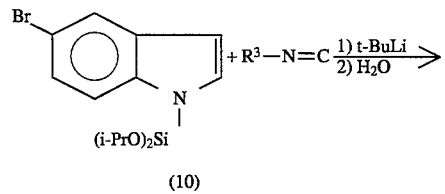

(A) 5-Bromo-1-tri(isopropyl)silyl-indole (10)

Sodium hydride (3.5 g) is stirred in DMF (50 mL) and cooled in an ice water bath. A solution of 5-bromoindole (10; 23.5 g) and TIPS-chloride (28 mL) in DMF (50 mL) is added dropwise to the stirring NaH suspension. The reaction is allowed to stir overnight while slowly warming to room temperature. The reaction is quenched with water and the layers are separated in a separatory funnel. The aqueous layer is extracted with $Et_2O$ (2×) and the combined organic fractions are washed with brine. The organic solution is dried over $MgSO_4$, filtered and the solvents are removed in vacuo. The product is purified by flash chromatography in 5% EtOAc/hexane to give 29 g (69%) of (10).

(B) To a 0.1 M solution of 5-bromo-1-tri(isopropyl)silyl-indole (10; 1 equiv) at −78° C. is added tert-butyllithium (1.2 equiv). The reaction is stirred for 15 min and the isocyanate (1.5 equiv) is swiftly added. The reaction is allowed to stir overnight while slowly warming to room temperature. The reaction is quenched with $H_2O$ and the layers are separated in a separatory funnel. The aqueous layer is extracted with $Et_2O$ (2×) and the combined organic fractions are washed with brine. The organic solution is dried over $MgSO_4$, filtered and the solvents are removed in vacuo. The crude reaction residue is dissolved in EtOH (0.1–0.2 M) and excess KF is added. The heterogeneous reaction is refluxed for 4 h and the EtOH is removed in vacuo. The reaction residue is then partitioned between EtOAc and $H_2O$. The layers are separated and the aqueous layer is extracted with EtOAc (2×). The organic solution is dried over $Na_2SO_4$, filtered and the solvent is removed in vacuo. Purification is by flash chromatography of the resulting residue in an EtOAc/hexane gradient to give the appropriate indolecarboxamide (11).

Synthesis of Product of Formula I

General Procedure for the Condensation of Indoles (III) with Cycloalkanones (II)

An appropriate indole (III; 1.0 equiv) and cycloalkanone (II; 1.0 to 2.0 equiv) are stirred in alcohol, preferably ethanol (20 mL/g of indole, II) under $N_2$. Pyrrolidine (2.5 equiv) is added and the reaction is refluxed for 18–48 hr utilizing TLC examination to indicate reaction completion. The Formula I products are recognizable on TLC due to their tendency to fluoresce in UV light as opposed to the reaction starting materials. Decomposition is indicated by the appearance of other dark blue spots (non fluorescent).

Working up the reaction is done by removal of solvent and excess pyrrolidine in vacuo. The residual oils are then purified by gradient flash chromatography using a 2–10% methanol in $CH_2Cl_2$ gradient system with an added 0.2% of $NH_4OH$. The purified base forms can be converted to acid salt forms utilizing standard salt-forming procedures.

This procedure is more fully demonstrated with several specific exemplifications.

EXAMPLE 17

N-Methyl-3-[[4-(2-phenylethyl)amino ]-1-cyclohexen-1-yl]-1H-indole-5-acetamide

N-Methyl-1H-indole-5-acetamide (0.86 g, 0.00457 mol), 4-[(2-phenylethyl)amino]cyclohexanone (1.49 g, 0.00686 mol) and pyrrolidine (3 mL) were dissolved in EtOH (10 mL) and heated at reflux for 24 h. The solvent was removed in vacuo. Silica gel chromatography (10–100% EtOAc gradient in hexane followed by 10–20% MeOH gradient in EtOAc) of the concentrate afforded the product (0.29 g, 16.3%). Treatment of this material with fumaric acid in MeOH afforded the fumarate salt which was recrystalized from EtOH/EtOAc (0.2 g, 58.3%): mp 225°–227° C. Anal. Calcd for $C_{25}H_{29}N_3O \cdot 0.5\ C_4H_4O_4$: C 70.78; H 7.13; N 9.17. Found: C 70.72; H 7.07; N 8.96.

EXAMPLE 18

5-Acetyl-3-[[4-[(2-phenylethyl)amino]]-1-cyclohexen-1-yl]-1H-indole

5-Acetyl-1-H-indole[1] (3.18 g, 0.02 mol), 4-[(2-phenylethyl)amino]cyclohexanone (5.2 g, 0.024 mol) and pyrrolidine (5 mL) were dissolved in EtOH (30 mL) and refluxed for 48 h. The solvent was removed in vacuo. Silica gel chromatography (20–100% EtOAc gradient in hexane followed by 5–20% MeOH gradient in EtOAc) of the residue yielded the product (6.93 g, 96%). Treatment of this material with fumaric acid in MeOH afforded the fumarate salt which was recrystallized from MeOH/EtOAc (2.6 g, 30.5%): mp 266°–269° C. Anal. Calcd for $C_{24}H_{26}N_2 \cdot 0.7\ C_4H_4O_4$: C 73.25; H 6.84; N 6.37. Found: C 73.20; H 6.60; N 6.37.

[1] Prepared according to the procedure reported in CA 54 12098e.

EXAMPLE 19

Methyl 3-[[4-(2-phenylethyl)amino]-1-cyclohexen-1-yl]-1H-indole-5-carboxylate Methyl 1H-indole-5-carboxylate[2] (1.75 g, 0.01 mol), 4-[(2-phenylethyl)amino]cyclohexanone (2.6 g, 0.012 mol) and pyrrolidine (5 mL) were dissolved in EtOH (20 mL) and refluxed for 24 h. The solvent was removed in vacuo. Silica gel chromatography (50–100% EtOAc gradient in hexane followd by 5–20% MeOH gradient in EtOAc) of the residue yielded the product (2.36 g, 63%). Treatment of 1.5 g of this material with fumaric acid in MeOH afforded the fumarate salt which was recrystallized from EtOH/EtOAc (0.47 g, 25.7%): mp 232°–235° C. Anal. Calcd for $C_{24}H_{26}N_2O_2 \cdot 0.7\ C_4H_4O_4$: C 70.63; H 6.37; N 6.15. Found: C 70.63; H 6.74; N 6.03.

[2] Prepared according to the procedure used by Ponticello and Baldwin, *J. Org. Chem.*; 1979, 44(22), 4001.

EXAMPLE 20

3-[[4-(2-Phenylethyl)amino]-1-cyclohexen-1-yl]1-H-indole-5-actamide 1H-indole-5-acetamide[3] (0.63 g, 0.0036 mol), 4-[(2-phenylethyl)amino]cyclohexanone (1.17 g, 0.0054 mol) and pyrrolidine (4 mL) were dissolved in EtOH (10 mL) and heated at reflux for 48 h. The solvent was removed in vacuo. Silica gel chromatography (using $CH_2Cl_2$:Methanol:$NH_4OH$; 95:4.5:0.5 followed by $CH_2Cl_2$:Methanol:$NH_4OH$; 90:9:1) of the concentrate afforded the product (1.01 g, 75%). Treatment of this material with fumaric acid in MeOH afforded the fumarate salt which was recrystallized from MeOH/EtOAc (0.9 g, 75.4%): mp 207°–210° C. Anal. Calcd for $C_{24}H_{27}N_3O \cdot 0.5\ C_4H_4O_4$: C 70.89; H 6.86; N 9.54. Found: C 70.61; H 6.71; N 9.29.

[3] Prepared from 4-nitrobenenamine and methylamino by analogy to the preparation of N-methyl-1H-indole-5-acetamide cited above.

Additional synthetic examples of Formula I products are listed in Table 2.

TABLE 1

Formula I Compound Synthetic Examples

| Ex # | R¹ | R² | m | n | p | Ar | Analytic Formula | mp (°C.) |
|---|---|---|---|---|---|---|---|---|
| 22 | H₂NCO | H | 0 | 2 | 0 | Ph | $C_{21}H_{21}N_3O$ | 184–6 |
| 23 | H₂NCO | H | 0 | 2 | 0 | f-Ph | $C_{21}H_{20}N_3OF$ | 209–11 |
| 24 | H₂NCO | H | 0 | 2 | 1 | Ph | $C_{22}H_{23}N_3O/0.2\ H_2O$ | 223(d) |
| 25 | H₂NCO | H | 0 | 2 | 2 | Ph | $C_{23}H_{25}N_3O/0.8\ HCl/0.9\ H_2O$ | 185(d) |
| 26 | MeNHCO | H | 0 | 2 | 2 | Ph | $C_{24}H_{27}N_3O/1.15\ H_2O$ | 182–3 |
| 27 | EtNHCO | H | 0 | 2 | 2 | Ph | $C_{25}H_{29}N_3O/H_2O$ | 136–9 |
| 28 | PhNHCO | H | 0 | 2 | 2 | Ph | $C_{29}H_{29}N_3O/0.5\ C_4H_4O_4/0.7\ H_2O$ | 225–7 |
| 29 | H₂NCO | H | 0 | 2 | 2 | o-F—Ph | $C_{23}H_{24}N_3OF/0.5\ C_4H_4O_4/0.3\ H_2O$ | >225 |
| 30 | H₂NCO | H | 0 | 2 | 2 | p-F—Ph | $C_{23}H_{24}N_3OF$ | 192–4 |
| 31 | H₂NCO | H | 0 | 2 | 2 | o-MeO—Ph | $C_{24}H_{27}N_3O_2/C_4H_4O_4$ | 209(d) |
| 32 | H₂NCO | H | 0 | 2 | 2 | p-MeO—Ph | $C_{24}H_{27}N_3O_2/0.5\ C_4H_4O_4/0.25\ H_2O$ | >225 |
| 33 | H₂NCO | H | 0 | 2 | 2 | 2-pyridinyl | $C_{22}H_{24}N_4O/0.5\ C_4H_4O_4$ | 194–6 |
| 34 | H₂NCO | H | 0 | 2 | 2 | 3-pyridinyl | $C_{22}H_{24}N_4O/0.7\ C_4H_4O_4/0.8\ H_2O$ | 197–9 |
| 35 | H₂NCO | H | 0 | 2 | 3 | Ph | $C_{24}H_{27}N_3O/0.5\ C_4H_4O_4$ | 189(d) |

Any of the cycloalkenyl products (IB) as synthesized above can be readily converted into cycloalkanyl products (IA) by standard hydrogenation procedures. IA compounds can exist as cis and trans ring isomers.

EXAMPLE 36

Cis and trans-3-[4-(N-(2-Phenylethyl)amino)cyclohexanyl]-1H-indole-5-carboxamide 3-[4-[N-(2-phenylethyl)amino]cyclohex-1-enyl]-1H-indole-5-carboxamide (IB, 2.57 g) is dissolved in 60 mL of ethanol. Palladium or carbon (1 g) is added to the solution and the reaction is shaken on a Parr hydrogenation apparatus under 50–55 psi of hydrogen until the IB compound is consumed (TLC monitor). More Pd/C may be required to complete the reaction which is then filtered through Celite, stripped to dryness and flash chromatographed in a 2 to 4% MeOH in $CH_2Cl_2$ (with 0.2% $NH_4OH$) gradient chromatography system. The two isomers are collected as A (higher $R_f$ value) and B (lower $R_f$ value). Conversion of isomer A (668 mg) to the hemifumarate salt with crystallization from EtOH gives:

3-[4-cis-[N-(2-phenylethyl)amino]cyclohex-1-anyl]-1H-indole-5-carboxamide hemifumarate ethanolate, mp>230°. $^1$H NMR (methanol-$d^4$) δ 8.22 (d, J=1.3 Hz, 1H), 7.65 (dd, J=8.6, 1.7 Hz, 1H), 7.39–7.22 (m, 7H), 6.68 (s, 1H), 3.60 (q, J=7.0 Hz, 0.7 H), 3.22 (m, 3H), 2.99 (m, 2H), 2.10 (m, 2H), 1.95 (m, 6H), 1.17 (t, J=7.0 Hz, 1H); IR (KBr) 1660, 1570, 1375 $cm^{-1}$; mass spectrum $[M+H]^+$ 362; Anal. calcd for $C_{23}H_{27}N_3O/0.5$ $C_4H_4O_4/0.3$ $C_2H_6O$: C, 70.96; H, 7.16; N, 9.70. Found: C, 70.90; H, 7.28; N, 9.65.

Conversion of isomer B (791 mg) to the hemifumarate salt with crystallization from EtOH gives:

3-[4-trans-[N-(2-phenylethyl)amino]cyclohex-1-anyl]-1H-indole-5-carboxamide hemifumarate hydrate, mp>230°. $^1$H NMR (methanol-$d^4$) δ 8.13 (d, J=1.2 Hz, 1H), 7.57 (dd, J=8.6, 1.7 Hz, 1H), 7.30–7.15 (m, 6H), 7.04 (s, 1H), 6.48 (s, 1H), 3.10 (m, 2H), 2.88 (m, 2H), 2.49 (m, 2H), 2.12 (m, 4H), 1.52 (m, 4H); IR (KBr) 1660, 1575, 1375 $cm^{-1}$; mass spectrum $[M+H]^+$ 362; Anal. calcd for $C_{23}H_{27}N_3O/0.5$ $C_4H_4O_4/0.8$ $H_2O$: C, 69.20; H, 7.11; N, 9.68; $H_2O$, 3.32. Found: C, 69.51; H, 6.86; N, 9.63; H20, 3.52.

In addition, a mixture of A and B was obtained; 645 mg, 25% yield.

We claim:

1. A compound of Formula I or a pharmaceutically acceptable acid addition salt or solvate thereof

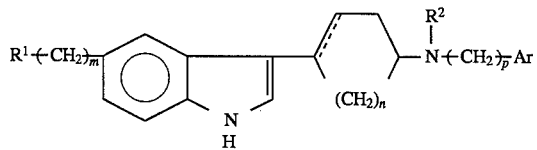

wherein
Ar is

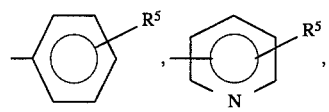

and

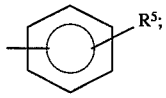

$R^1$ is a substituent selected from $—COR^2$, $—CONHR^3$, $—CO_2R^4$, $—OH$, $—NR^2COR^4$, $—NR^2SO_2R^3$, $—SO_2R^4$, and $—SO_2NHR^3$, with the proviso that $R^1$ is not $CONHR^3$ when Ar is

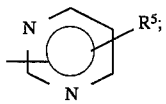

$R^2$ is hydrogen and lower alkyl;

$R^3$ is hydrogen, lower alkyl and phenyl-lower-alkylene;

$R^4$ is lower alkyl;

$R^5$ is hydrogen, halogen, or lower alkoxy;

m is zero or 1;

n is an integer from 1 to 3;

p is zero or an integer from 1 to 4; and the solid and dotted line represent either a single or double covalent bond.

2. A compound of claim 1 wherein $R^1$ is $—CONHR^3$.

3. A compound of claim 1 wherein n is 2.

4. A compound of claim 1 wherein Ar is

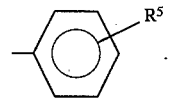

5. A compound of claim 2 selected from the group consisting of 3-[4-[N-[2-(pyridin-2-yl)ethyl]amino]cyclohexen-1-yl]-1H-indole-5-carboxamide and 3-[4-[N-[2-pyridin-3-yl)ethyl]amino]cyclohexen-1-yl]-1H-indole-5-carboxamide.

6. A compound of claim 1 selected from the group consisting of 5-acetyl-3-[4-[N-(2-phenylethyl)amino]cyclohexen-1-yl]-1H-indole and 5-carboxymethyl-3-[4-[N-(2-phenylethyl)amino]cyclohexen-1-yl]-1H-indole.

7. The method for treating vascular headaches by administering a therapeutically effective amount of a compound claimed in claim 1 to a person suffering from a vascular headache.

8. A pharmaceutical composition in unit dosage form suitable for systemic administration to a person at risk of or suffering a vascular headache, the composition comprising a pharmaceutical carrier and from about 1 to 500 mg of a compound claimed in claim 1.

* * * * *